(12) United States Patent
Resh et al.

(10) Patent No.: US 9,943,507 B2
(45) Date of Patent: Apr. 17, 2018

(54) TREATMENT OF PANCREATIC AND RELATED CANCERS WITH 5-ACYL-6,7-DIHYDROTHIENO[3,2-C] PYRIDINES

(71) Applicants: Memorial Sloan-Kettering Cancer Center, New York, NY (US); The Rockefeller University, New York, NY (US)

(72) Inventors: Marilyn D. Resh, New York, NY (US); Joseph Fraser Glickman, New York, NY (US); Elissaveta Petrova, New York, NY (US); Ouathek Ouerfelli, Fort Lee, NY (US)

(73) Assignees: Memorial Sloan-Kettering Cancer Center, New York, NY (US); The Rockefeller University, New York, NY (US)

( * ) Notice: Subject to any disclaimer, the term of this patent is extended or adjusted under 35 U.S.C. 154(b) by 0 days.

(21) Appl. No.: 15/459,911

(22) Filed: Mar. 15, 2017

(65) Prior Publication Data
US 2017/0252328 A1 Sep. 7, 2017

Related U.S. Application Data (62) Division of application No. 15/004,847, filed on Jan. 22, 2016, now Pat. No. 9,597,320, which is a division of application No. 14/387,033, filed as application No. PCT/US2013/031311 on Mar. 14, 2013, now Pat. No. 9,242,994.

(60) Provisional application No. 61/614,954, filed on Mar. 23, 2012.

(51) Int. Cl.
| | | |
|---|---|---|
| C07D 513/02 | (2006.01) | |
| A61K 31/4365 | (2006.01) | |
| C07D 495/04 | (2006.01) | |

(52) U.S. Cl.
CPC ........ A61K 31/4365 (2013.01); C07D 495/04 (2013.01)

(58) Field of Classification Search
CPC ................................................ A61K 31/4365
USPC ....................................................... 546/114
See application file for complete search history.

(56) References Cited

U.S. PATENT DOCUMENTS

| 4,075,340 | A | 2/1978 | Maffrand | |
|---|---|---|---|---|
| 4,749,692 | A | 6/1988 | Blanchard et al. | |
| 9,242,994 | B2 * | 1/2016 | Resh | C07D 495/04 |
| 9,597,320 | B2 * | 3/2017 | Resh | A61K 31/4365 |
| 2009/0054452 | A1 | 2/2009 | Eggenweiler et al. | |
| 2009/0197864 | A1 | 8/2009 | Li et al. | |

FOREIGN PATENT DOCUMENTS

| AU | 2006220095 A1 | 9/2006 |
|---|---|---|
| DE | 102010013716 A1 | 10/2011 |
| JP | 2001514631 A | 9/2001 |
| JP | 2011516515 A | 5/2011 |
| RU | 2007 136 165 A | 4/2009 |
| WO | WO 1998/40385 A1 | 9/1998 |
| WO | WO 2008/143263 A1 | 11/2008 |
| WO | WO 2009/073203 A1 | 6/2009 |
| WO | WO 2009/124746 A1 | 10/2009 |
| WO | WO 2010/046108 A1 | 4/2010 |
| WO | WO 2010/101230 A1 | 9/2010 |
| WO | WO 2011/020849 A1 | 2/2011 |

OTHER PUBLICATIONS

Rodgers, ACS Chem. Biol. 2016, 11, 3256-3262.*
International Search Report and Written Opinion for Application No. PCT/US2013/031311, dated Aug. 29, 2013.
International Preliminary Report on Patentability for Application No. PCT/US2013/031311, dated Oct. 2, 2014.
[No Author Listed] CHEMCATS Compounds RN 1193221-41-8, 1172558-42-7, 1171566-25-8, 1171537-35-1, 1171533-62-2, 1171509-19-5, 1171472-51-7 , 1170797-08-6, 1170388-89-2, 1170157-72-8, 1048204-83-6, 1048190-35-7, 1047084-42-3, 1046592-94-2, 1023803-93-1, 1023439-77-1, 1022808-90-7. STN on the Web. Sep. 1, 2016.
[No Author Listed], CHEMCATS Compounds RN 861702-25-2, 861690-87-1, 859483-56-0, 859463-74-4, 859359-93-6, 859345-25-8, 859103-03-0, 859090-68-9, 859089-20-6, 858921-78-5, 858543-73-4, 858334-53-9, 858328-95-7, 858113-67-4, 858064-95-6, 858052-18-3, 858051-19-1, 857876-88-1, 857876-47-2, 857861-33-7, 857848-71-6, 857666-87-6, 857662-77-2, 857656-77-0, 856146-70-8, 856127-26-9, 855668-49-4, 855459-54-0, 855187-86-9, 855148-10-6, 855135-88-5, 855132-50-2, 854993-61-6, 854979-91-2, 854953-90-5, 854949-30-7, 854946-19-3, 854619-76-4, 854603-78-4, 854540-97-9, 854539-54-1 854186-01-9, 854096-37-0, 854076-84-9, 85377800-4, 853722-56-2, 853633-00-8, 853392-98-0, 853370-02-2, 853365-39-6, 853365-30-7, 853344-99-7, 853230-63-4, 858911-43-0, 858894-89-0. STN on the Web. Jun.-Aug. 2005 23 pages.
Alibek et al., The role of infectious agents in urogenital cancers. Infect Agent Cancer. Dec. 3, 2012;7(1):35. doi:10.1186/1750-9378-7-35.

(Continued)

Primary Examiner — Nizal Chandrakumar
(74) Attorney, Agent, or Firm — Wolf, Greenfield & Sacks, P.C.

(57) ABSTRACT

Methods for inhibiting the growth of pancreatic cancer cells or other cancer cells driven by Sonic hedgehog are disclosed. The method involves exposing the cells to 5-acyl-6,7-dihydrothieno[3,2-c]pyridines of formula I

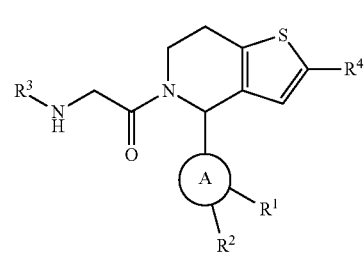

20 Claims, 3 Drawing Sheets

(56) References Cited

OTHER PUBLICATIONS

Ballell et al., Fueling open-source drug discovery: 177 small-molecule leads against tuberculosis. ChemMedChem. Feb. 2013;8(2):313-21. doi: 10.1002/cmdc.201200428. Epub Jan. 10, 2013.

Barreca et al., Pharmacophore modeling as an efficient tool in the discovery of novel noncompetitive AMPA receptor antagonists. J Chem Inf Comput Sci. Mar.-Apr. 2003;43(2):651-5.

Batsaikhan et al., Cyclopamine decreased the expression of Sonic Hedgehog and its downstream genes in colon cancer stem cells. Anticancer Res. Nov. 2014;34(11):6339-44.

Berthiaume et al., Synthesis and use of iodo-fatty acid analogs. Methods Enzymol. 1995;250:454-66.

Buglino et al., Identification of conserved regions and residues within Hedgehog acyltransferase critical for palmitoylation of Sonic Hedgehog. PLoS One. Jun. 23, 010;5(6):e11195. doi: 10.1371/journal.pone.0011195.

Buglino et al., What is a palmitoylacyltransferase with specificity for N-palmitoylation of Sonic Hedgehog. J Biol Chem. Aug. 8, 2008;283(32):22076-88. doi: 10.1074/jbc.M803901200. Epub Jun. 4, 2008.

Dormoy et al., The sonic hedgehog signaling pathway is reactivated in human renal cell carcinoma and plays orchestral role in tumor growth. Mol Cancer. Dec. 16, 2009;8:123. doi: 10.1186/1476-4598-8-123.

Ertao et al., Autocrine Sonic hedgehog signaling promotes gastric cancer proliferation through induction of phospholipase Cγl and the ERK1/2 pathway. J Exp Clin Cancer Res. Apr. 2, 2016;35:63. doi: 10.1186/s13046-016-0336-9.

Feldmann et al., Blockade of hedgehog signaling inhibits pancreatic cancer invasion and metastases: a new paradigm for combination therapy in solid cancers. Cancer Res. Mar. 1, 2007;67(5):2187-96.

Foloppe et al., Discovery and functional evaluation of diverse novel human CB(1) receptor ligands. Bioorg Med Chem Lett. Aug. 1, 2009;19(15):4183-90. doi: 10.1016/j.bmcl.2009.05.114. Epub Jun. 2, 2009.

Hallahan et al., SmoA1 mouse model reveals that notch signaling is critical for the growth and survival of sonic hedgehog-induced medulloblastomas. Cancer Res. Nov. 1, 2004;64(21):7794-800.

Huang et al., Activation of the hedgehog pathway in human hepatocellular carcinomas. Carcinogenesis. Jul. 2006;27(7):1334-40. Epub Feb. 25, 2006.

Lanyon-Hogg et al., Click chemistry armed enzyme-linked immunosorbent assay to measure palmitoylation by hedgehog acyltransferase. Anal Biochem. Dec. 1, 2015;490:66-72. doi: 10.1016/j.ab.2015.08.025. Epub Sep. 1, 2015.

Lupi, Correlations between the Sonic Hedgehog pathway and basal cell carcinoma. Int J Dermatol. Nov. 2007;46(11):1113-7.

Madsen et al., Glucose-6-phosphatase catalytic enzyme inhibitors: synthesis and in vitro evaluation of novel 4,5,6,7-tetrahydrothieno[3,2-c]- and [2,3-c]pyridines. Bioorg Med Chem. Sep. 2000;8(9):2277-89.

Morton et al., Shh signaling and pancreatic cancer: implications for therapy? Cell Cycle. Jul. 1, 2007;6(13):1553-7. Epub May 18, 2007. Review.

Nguyen et al., Novel signaling pathways in osteosarcoma. Int J. Orthopaedics. Oct. 23, 2014;1(3):73-84.

Olive et al., Inhibition of Hedgehog signaling enhances delivery of chemotherapy in a mouse model of pancreatic cancer. Science. Jun. 12, 2009;324(5933):1457-61. doi: 10.1126/science.1171362. Epub Dec. 7, 2009. 10 pages.

Oro et al., Basal cell carcinomas in mice overexpressing sonic hedgehog. Science. May 2, 1997;276(5313):817-21.

Pasca Di Magliano et al., Hedgehog signalling in cancer formation and maintenance. Nat Rev Cancer. Dec. 2003;3(12):903-11. Review.

Peseckis et al., Iodinated fatty acids as probes for myristate processing and function. Incorporation into pp60v-src. J Biol Chem. Mar. 5, 1993;268(7):5107-14.

Petrova et al., Inhibitors of Hedgehog acyltransferase block Sonic Hedgehog signaling. Nat Chem Biol. Apr. 2013;9(4):247-9. doi: 10.1038/nchembio.1184. Epub Feb. 17, 2013.

Samarzija et al., Hedgehog pathway regulators influence cervical cancer cell proliferation, survival and migration. Biochem Biophys Res Commun. Aug. 17, 2012;425(1):64-9. doi: 10.1016/j.bbrc.2012.07.051. Epub Jul. 20, 2012.

Sanchez et al., Inhibition of prostate cancer proliferation by interference with SONIC HEDGEHOG-GLI1 signaling. Proc Natl Acad Sci U S A. Aug. 24, 2004;101(34):12561-6. Epub Aug. 16, 2004.

Subramani et al., Gedunin inhibits pancreatic cancer by altering sonic hedgehog signaling pathway. Oncotarget. Mar. 14, 2016. doi: 10.18632/oncotarget.8055. [Epub ahead of print].

Szkandera et al., Hedgehog signaling pathway in ovarian cancer. Int J Mol Sci. Jan. 9, 2013;14(1):1179-96. doi:10.3390/ijms14011179.

Tamayo et al., Fused piperidines as a novel class of potent and orally available transient receptor potential melastatin type 8 (TRPM8) antagonists. J Med Chem. Feb. 23, 2012;55(4):1593-611. doi: 10.1021/jm2013634. Epub Feb. 13, 2012. 19 pages.

Wang et al., Three-dimensional quantitative structure—activity relationship of 4,5,6,7-tetrahydrothienopyridines analogues as glucose-6-phosphatase inhibitors. J Mol. Structure. Jan. 2006;782(1):49-54.

Watkins et al., Hedgehog signalling within airway epithelial progenitors and in small-cell lung cancer. Nature. Mar. 20, 2003;422(6929):313-7. Epub Mar. 5, 2003.

* cited by examiner

TREATMENT OF PANCREATIC AND RELATED CANCERS WITH 5-ACYL-6,7-DIHYDROTHIENO[3,2-C] PYRIDINES

CROSS-REFERENCE TO RELATED APPLICATIONS

This application is a divisional of and claims priority under 35 U.S.C. § 120 to U.S. Application, U.S. Ser. No. 15/004,847, filed Jan. 22, 2016, which is a divisional of and claims priority under 35 U.S.C. § 120 to U.S. application, U.S. Ser. No. 14/387,033, filed Sep. 22, 2014, which is a national stage filing under 35 U.S.C. § 371 of international PCT application, PCT/US2013/031311, filed Mar. 14, 2013, which claims priority under 35 U.S.C. § 119(e) to U.S. Provisional Patent Application, U.S. Ser. No. 61/614,954, filed Mar. 23, 2012, each of which is hereby incorporated herein by reference.

STATEMENT AS TO RIGHTS UNDER FEDERALLY-SPONSORED RESEARCH

This invention was made with Government support under Contracts Nos. GM57966 and CA158474, awarded by the National Institutes of Health. Accordingly, the U.S. Government has certain rights in this invention.

FIELD OF THE INVENTION

The invention relates to 5-acyl-6,7-dihydrothieno[3,2-c] pyridines that are useful for treating pancreatic cancer and other types of cancers that are associated with aberrant expression of Hedgehog proteins.

BACKGROUND OF THE INVENTION

Pancreatic cancer is the fourth most common cause of cancer death in the world, and it has a poor prognosis. For all stages combined, the 1- and 5-year relative survival rates are 25% and 6%, respectively; the median survival for locally advanced and for metastatic disease, which collectively represent over 80% of individuals, is about 10 and 6 months respectively. It is estimated that in the United States in 2012 there will be 43,920 new cases and 37,390 deaths.

Hedgehog (Hh) and Sonic Hedgehog (Shh) are signaling proteins that mediate growth and patterning during embryonic development. These proteins act as morphogens to form long and short range signaling gradients. Hh is expressed in flies, while vertebrates express 3 family members: Sonic, Indian and Desert, of which Shh is the best studied. Shh regulates limb development, cell proliferation and differentiation. In adult tissues, aberrant Shh expression or signaling is implicated in the biogenesis of multiple human cancers, including medulloblastoma, basal cell carcinoma, liver, pancreatic and urogenital tumors [See Pasca di Magliano, M., and Hebrok, M. (2003) Hedgehog signalling in cancer formation and maintenance, Nat Rev Cancer 3, 903-911.]

Hedgehog proteins undergo a unique set of post-translational processing reactions. Shh is synthesized as a 45 kDa precursor that traffics through the secretory pathway. After the signal sequence is removed, Shh undergoes autocleavage to generate a 19 kDa N-terminal signaling molecule, ShhN. During this reaction, cholesterol is attached to the C-terminus of ShhN. In addition, the N-terminal cysteine residue of ShhN is modified by palmitoylation. Unlike nearly all other known palmitoylated proteins, palmitate is attached via an amide bond to the N-terminus of ShhN. Palmitoylation of Hh and Shh is critical for effective long- and short-range signaling. Mutation of the N-terminal Cys to Ser or Ala results in a mutant protein with little or no activity in vivo or in vitro. Attachment of palmitate to Shh is catalyzed by the multipass membrane protein Hhat (Hedgehog acyltransferase). Hhat is a member of the membrane-bound O-acyl transferase (MBOAT) family. Most MBOAT family members catalyze transfer of long chain fatty acids to hydroxyl groups of lipids; however, Hhat is one of three MBOAT proteins that transfer fatty acids to protein substrates. In each case, fatty acid modification of the substrate protein is essential for its signaling function.

The normal adult pancreas does not express Shh. However, aberrant Shh expression can occur in the mature pancreas, where it plays a critical role in promoting pancreatic cancer [See Morton, J. P., and Lewis, B. C. (2007) "Shh signaling and pancreatic cancer: implications for therapy?", Cell Cycle 6, 1553-1557.] Aberrant expression of Shh drives proliferation of pancreatic cancer cells and formation of pancreatic intraepithelial neoplasms, and Hedgehog signaling is one of the core pathways altered in all human pancreatic cancers. Mouse models of pancreatic cancer reveal that Shh functions synergistically with activated K-Ras to promote and maintain tumorigenesis, while inhibition of Shh signaling blocks pancreatic cancer invasion and metastasis [See Olive et al. (2009) "Inhibition of Hedgehog signaling enhances delivery of chemotherapy in a mouse model of pancreatic cancer", Science 324, 1457-1461 and Feldmann et al. (2007) "Blockade of hedgehog signaling inhibits pancreatic cancer invasion and metastases: a new paradigm for combination therapy in solid cancers", Cancer Res. 67, 2187-2196.]

There is an urgent need for novel therapeutics to treat pancreatic cancer. We describe herein Hhat inhibitors that block Shh palmitoylation, and thus provide opportunities for efficacious treatment of pancreatic cancer.

SUMMARY OF THE INVENTION

The compounds of the invention are useful as anticancer agents, particularly in the treatment of Shh-driven cancers such as pancreatic cancer, gastric cancer, colon cancer, prostate cancer, osteosarcoma and small cell lung cancer.

In one aspect, the invention relates to a compound of formula I wherein
$R^1$ and $R^2$ are independently selected from H, halogen, $(C_1\text{-}C_4)$hydrocarbyl, $(C_1\text{-}C_4)$alkoxy, trifluoromethyl, trifluoromethoxy, cyano and nitro;
$R^3$ is selected from $(C_1\text{-}C_{10})$hydrocarbyl, $(C_1\text{-}C_6)$oxaalkyl and heterocyclylalkyl; and
$R^4$ is selected from H, methyl, halomethyl, dihalomethyl, and trihalomethyl.

In another aspect, the invention relates to a pharmaceutical composition comprising a pharmaceutically acceptable carrier and a compound of formula I.

In another aspect, the invention relates to a method for treating an Shh-driven cancer comprising administering to a patient having such a cancer a therapeutically effective amount of a compound of formula I.

DETAILED DESCRIPTION OF THE INVENTION

In a composition aspect, the invention relates to a compound of formula I

I as described above. In some embodiments, A is chosen from pyrrolidine, furan, thiophene and pyridine. In some embodiments, $R^1$ may be H and $R^2$ may be H or methyl. In other embodiments, A is phenyl. In these embodiments, $R^1$ may be ortho relative to the point of attachment of phenyl to the thieno[3,2-c]pyridine and $R^2$ may be para to the point of attachment of phenyl to the thieno[3,2-c]pyridine. Such compounds would be represented by formula II:

II

In some of these compounds, $R^1$ may be H or methyl and $R^2$ may be chosen from H, methyl, methoxy, chloro and fluoro. In others, $R^1$ and $R^2$ may be the same and may be chosen from H and halogen.

In some embodiments, $R^3$ may be selected from $(C_1-C_{10})$alkyl, $(C_1-C_6)$oxaalkyl and heterocyclylalkyl. In some embodiments, $R^3$ may be chosen from $(C_3-C_6)$alkyl, $(C_3-C_6)$alkenyl, $(C_3-C_6)$cycloalkyl, $(C_1-C_6)$oxaalkyl, furanyl$(C_1-C_4)$alkyl, thienyl$(C_1-C_4)$alkyl, pyrrolyl$(C_1-C_4)$alkyl, pyrrolidinyl$(C_1-C_4)$alkyl and tetrahydrofuranyl$(C_1-C_4)$alkyl. In particular examples, $R^3$ is methoxyethyl, methoxypropyl, ethoxypropyl, isopropyl, cyclopropyl, allyl or furanylmethyl.

In some embodiments, $R^4$ is hydrogen.

Throughout this specification the terms and substituents retain their definitions.

Alkyl is intended to include linear or branched saturated hydrocarbon structures. Examples of alkyl groups include methyl, ethyl, propyl, isopropyl, butyl, s- and t-butyl, 1-methyl-3-ethyloctyl and the like. Preferred alkyl groups are those of $C_{20}$ or below.

Cycloalkyl is for the purposes herein distinguished from alkyl and includes cyclic hydrocarbon groups of from 3 to 10 carbon atoms. Examples of cycloalkyl groups include c-propyl, c-butyl, c-pentyl, norbornyl, decahydronaphthyl and the like.

Alkoxy or alkoxyl refers to groups of from 1 to 8 carbon atoms of a straight or branched configuration attached to the parent structure through an oxygen. Examples include methoxy, ethoxy, propoxy, isopropoxy and the like.

Aryl and heteroaryl generally refer to a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. In the embodiments described herein, the ring A is limited to 5- or 6-membered aromatic or heteroaromatic rings such as benzene, pyrrole, imidazole, pyridine, thiophene, thiazole, isothiazole, oxazole, isoxazole, furan, pyrimidine, pyrazine, tetrazole and pyrazole.

Arylalkyl means an aryl ring attached to an alkyl residue in which the point of attachment to the parent structure is through the alkyl. Examples are benzyl, phenethyl and the like. Heteroarylalkyl means an alkyl residue attached to a heteroaryl ring. Examples include, e.g., pyridinylmethyl, pyrimidinylethyl and the like.

$C_1$ to $C_{10}$ hydrocarbon (or, when describing a substituent, hydrocarbyl) means a linear, branched, or cyclic residue comprised of hydrogen and carbon as the only elemental constituents. The term includes alkyl, cycloalkyl, polycycloalkyl, alkenyl, alkynyl, aryl and combinations thereof. Examples include benzyl, phenethyl, cyclohexylmethyl, cyclopropylmethyl, cyclobutylmethyl, allyl, camphoryl and naphthylethyl.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, benzene and cyclohexene; $(C_8-C_{12})$ carbopolycycle refers to such systems as norbornane, decalin, indane and naphthalene. Carbocycle, if not otherwise limited, refers to monocycles, bicycles and polycycles.

Heterocycle means a cycloalkyl or aryl residue in which one to two of the carbons is replaced by a heteroatom such as oxygen, nitrogen or sulfur. Heteroaryls form a subset of heterocycles. Examples of heterocycles include pyrrolidine, pyrazole, pyrrole, imidazole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, pyrazine, thiophene, furan, oxazole, oxazoline, isoxazole, dioxane, tetrahydrofuran and the like.

As used herein, the term "optionally substituted" may be used interchangeably with "unsubstituted or substituted". The term "substituted" refers to the replacement of one or more hydrogen atoms in a specified group with a specified radical. Substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, hydroxy, loweralkoxy, haloalkoxy, oxaalkyl, carboxy, nitro, amino, alkylamino, and/or dialkylamino. In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

The compounds described herein may contain, in a substituent $R^x$, double bonds and may also contain other centers of geometric asymmetry; unless specified otherwise, it is intended that the compounds include both E and Z geometric isomers. Likewise, all tautomeric forms are also intended to be included. The compounds possess an asymmetric center at C-4 and may contain, in a substituent $R^x$, additional asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques.

As used herein, and as would be understood by the person of skill in the art, the recitation of "a compound"—unless expressly further limited—is intended to include salts of that compound. In a particular embodiment, the term "compound of formula I" refers to the compound or a pharmaceutically acceptable salt thereof.

The term "pharmaceutically acceptable salt" refers to salts whose counter ion (anion) derives from pharmaceutically acceptable non-toxic acids including inorganic acids and organic acids. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^{2}H$, $^{3}H$, $^{11}C$, $^{13}C$, $^{14}C$, $^{15}N$, $^{35}S$, $^{18}F$, $^{36}Cl$, $^{125}I$, $^{124}I$ and $^{131}I$ respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in Schemes 1 and 2 by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. In a first aspect, the invention relates to compounds; in a second aspect the invention relates to pharmaceutical compositions; in a third aspect, the invention relates to methods. Both the second aspect of the invention and the third aspect envision the use of any and all compounds of the formula I in the method of treatment. However, due to the peculiarities of patent law, and having nothing whatever to do with the scope of the inventors' conception of the invention, certain compounds appear from a preliminary search of the literature ineligible to be claimed as compounds. Thus, for example, compounds in which $R^3$ is cyclopropyl, $R^4$ is H and A is 4-t-butylphenyl, 4-methoxyphenyl, 4-methylphenyl, 2-methylphenyl, 4-chlorophenyl, phenyl, 4-fluorophenyl or 2,4-dichlorophenyl appear to be known. Similarly, compounds in which $R^3$ is cyclohexyl, $R^4$ is H and A is 2-methylphenyl or 2,4-dichlorophenyl appear to be known. In all of these cases, the compounds are disclosed in Chemical Abstracts only as members of a library, with no disclosed utility. Therefore, while these compounds are part of the inventive concept, they have been excluded from the claims to compounds, per se. It may be found upon further examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus I that are not already in the possession of the public.

While it may be possible for the compounds of formula I to be administered as the raw chemical, it is preferable to present them as a pharmaceutical composition. According to a further aspect, the present invention provides a pharmaceutical composition comprising a compound of formula I or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, intraperitoneally, intratumorally or subcutaneously.

Formulations include those suitable for oral, parenteral (including subcutaneous, intradermal, intramuscular, intravenous and intraarticular), rectal and topical administration. The compounds are preferably administered orally or by injection (intravenous, intramuscular, intraperitoneally, intratumorally or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose or multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient reporting one or more of the physiological symptoms of a disease, even though a diagnosis of this disease may not have been made.

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The compounds employed in the methods and pharmaceutical compositions described above are commercially available or may be synthesized by processes known in the art. In general, the synthesis may be schematically described as in Schemes 1 and 2. An aromatic aldehyde is reacted with an aminoethylthiophene under Pictet-Spengler conditions to provide an 4-aryl-4,5,6,7-tetrahydrothieno[3,2-c]pyridine. Alternatively, an aromatic acid may be reacted with an aminoethylthiophene to provide the amide and the amide reacted under Bischler-Napieralski conditions to provide the 4-aryl-6,7-dihydrothieno[3,2-c]pyridine, which is reduced with a borohydride reagent to provide the 4-aryl-4,5,6,7-tetrahydrothieno[3,2-c]pyridine. Both these routes are described in Madsen et al. *Bioorg. Med. Chem.* 8, 2277-2289 (2000), which is incorporated herein by reference.

The 4-aryl-4,5,6,7-tetrahydrothieno[3,2-c]pyridine may then be reacted with an activated glycine derivative (the acyl component) by any of the many means well known in the art, particularly in the art of the synthesis of peptides. Such agents include carbodiimides of various sorts, mixed anhydrides, EEDQ, HATU, and the like. It is also possible to pre-react the carboxylic acid with an appropriate leaving group to form an activated ester. Activated esters denote esters which are capable of undergoing a substitution reaction with the secondary amine to form an amide. The term includes esters "activated" by neighboring electron withdrawing substituents. Examples include esters of phenols, particularly electronegatively substituted phenol esters such as pentafluorophenol esters; O-esters of isourea, such as arise from interaction with carbodiimides; O-esters of N-hydroxyimides and N-hydroxy heterocycles; specific examples include S-t-butyl esters, S-phenyl esters, S-2-pyridyl esters, N-hydroxypiperidine esters, N-hydroxysuccinimide esters, N-hydroxyphthalimide esters and N-hydroxybenzotriazole esters. The carboxyl may also be activated by pre-reaction to provide acyl halides, such as acid chlorides and fluorides.

During condensation, the activated glycine will usually be protected with one of the common protecting groups, $R^{10}$, known in the peptide art. The protecting group, when present, will then be cleaved with a suitable cleaving agent to provide the 5-acyl-6,7-dihydrothieno[3,2-c]pyridines of formula I. Protecting groups for the amine are discussed in standard textbooks in the field of chemistry, such as Protec- tive Groups in Organic Synthesis by T. W. Greene and P. G. M. Wuts [John Wiley & Sons, New York, 1999], which is incorporated herein by reference. Particular attention is drawn to the chapter entitled "Protection for the Amino Group" (pages 494-614). Common protecting groups include, t-Boc, Fmoc and the like. Cleavage of t-Boc is accomplished by treatment with an acid, usually trifluoroacetic acid; cleavage of Fmoc is usually accomplished by treatment with a nucleophile such as piperidine or tetrabutylammonium fluoride.

SCHEME 1

SCHEME 2

-continued

I

Fourteen examples of compounds of the genus I have been prepared and tested according to the protocol described below.

Radioiodination of iodo-palmitate with [$^{125}$I] NaI and synthesis of $^{125}$I-iodo-palmitoyl and 3H-palmitoyl CoA derivatives using CoA synthetase were carried out as described by Berthiaume, L., et al. "Synthesis and use of iodo-fatty acid analogs". Methods Enzymol. 250, 454-466 (1995) and Peseckis, S. M., et al. (1993) "Iodinated fatty acids as probes for myristate processing and function. Incorporation into pp60v-src". J. Biol. Chem. 268, 5107-5114. The final concentrations of purified $^{125}$I-iodo-palmitoyl CoA and $^3$H-palmitoyl CoA, were determined from the absorbance at 260 nm using the extinction coefficient for palmitoylCoA.

A cell based assay was used to monitor Shh palmitoylation. COS-1 cells expressing Shh, Fyn, or ShhGFP fusions and Hhat were starved for 1 hr in DMEM containing 2% dialysed fetal calf serum, followed by incubation with 10-20 µCi/mL [$^{125}$I] IC16 or 4 hrs at 37 C. Cells were washed twice with 2 ml of ice cold STE (100 mM NaCl, 10 mM Tris, 1 mM EDTA [pH 7.4]) and lysed in 500 µl of RIPA Buffer (150 mM NaCl, 50 mM Tris, pH 7.4, 1% Triton X-100, 0.5% sodium deoxycholate, 0.1% SDS, 1 mM EDTA). Lysates were clarified by ultracentrifugation at 100,000×g for 15 min in a T100.2 rotor (Beckman, Fullerton, Calif.). Protein levels were determined by SDS-PAGE and Western blot analysis. Immunoprecipitations were performed by incubating clarified lysates with 5 µl of the appropriate antibody and 50 µl of protein A/G+ agarose beads (Santa Cruz Biotechnology) at 4° C. for 16 hrs. The beads were washed twice with 500 µl of RIPA buffer. The final bead pellets were resuspended in 40 µl of 2×SDS-PAGE sample buffer containing 40 mM DTT. Immunoprecipitated samples were run on a 12.5% SDS-PAGE gel, dried, and exposed by phosphorimaging for 2-3 days. Screens were analyzed on a FLA-7000 phosphorimager (Fuji). Labelings were performed in duplicate and repeated three times. For hydroxylamine treatment, gels were soaked in either 1M Tris or hydroxylamine, pH 8.0 for 1 hr, then dried and analyzed as above.

Expression and purification of recombinant Shh were carried out as described in Buglino, J. A. and Resh, M. D. "Hhat is a palmitoylacyl transferase with specificity for N-palmitoylation of sonic hedgehog". J. Biol. Chem. 283, 22076-22088 (2008) and Buglino, J. A. and Resh, M. D. "Identification of conserved regions and residues within Hedgehog acyltransferase critical for palmitoylation of Sonic Hedgehog". PLoS One 5, e11195 (2010). N-terminally 6×His tagged human Shh 24-197 with an enterokinase cleavage site immediately upstream of residue 24 was amplified using full length Shh as a template. The purified PCR product was ligated in NcoI and BamHI cut PET19b (Novagen). C24S and C24A constructs were generated by site directed mutagenesis using the Quick Change mutagenesis kit. All mutations were confirmed by sequencing. His-tagged Shh24-197 constructs were expressed in E. coli BL21(DE3) codon plus (Novagen), purified on Ni-NTA-agarose resin (Qiagen), and dialyzed (20 mM Tris-HCl, pH 8.0, 350 mM NaCl, 1 mM β-mercaptoethanol) in the presence of enterokinase (New England Biolabs). The dialyzed product was further purified by size exclusion chromatography on a Superdex 75 column (GE Heathcare). Pooled fractions after size exclusion chromatography were concentrated to 3.0-3.5 mg/ml in 20 mM HEPES, pH 7.3, 100 mM NaCl, 1 mM DTT. Protein concentration was measured using the DC protein assay (BioRad). The N-terminii of both wild type and mutant proteins were confirmed by Edman degradation.

HhatHAFlagHis was purified as follows. 20×100 mm plates of 293FT cells were transfected with HhatHAFlagHis or pcDNA3.1 empty vector. 48 hrs post transfection, the cells were placed on ice, washed twice with 5 ml of ice cold STE, and then scraped into 5 ml of STE per plate. Cells were pelleted by centrifugation at 1000×G for 10 min. Cell pellets were resuspended in 8 ml of cold hypotonic lysis buffer (0.2 mM MgCl2, 10 mM HEPES, pH 7.3). After 15 min incubation on ice, cells were lysed by 30 up/down strokes in a Dounce homogenizer with a tight fitting pestle. After lysis, 2 ml of 1.25M sucrose was added to yield 10 ml of total cell lysate. The lysate was separated into soluble (S100) and membrane (P100) fractions by ultracentrifugation at 100,000×G for 45 min in a Ti 70.1 fixed angle rotor (Beckman). After centrifugation, the supernatant was saved and the P100 pellets were resuspended in 10 ml of Hypotonic Lysis Buffer plus 0.25M sucrose and recentrifuged as above. The resultant supernatant was combined with the supernatant from the first spin for a total of 20 ml S100. The P100 membranes were again resuspended in 10 ml hypotonic lysis buffer+ 0.25M sucrose and recentrifuged as above. The supernatant was discarded and the pellets were resuspended in 10 ml of wash/solubilization buffer (20 mM HEPES, pH 7.3, 350 mM NaCl, 1% octylglucoside, 1% glycerol) and incubated on ice for 1 hr, followed by centrifugation at 100,000×g. The resultant pellet was discarded and the supernatant (detergent soluble fraction) was transferred to a 15 ml tube and 500 ml of Flag M2 resin (Sigma) was added. Following a 1 hr incubation, the Flag resin was pelleted by centrifugation at 1000×g and washed 4 times with 5 ml of solubilization/wash buffer. HhatHAFlagHis was eluted with 1.5 ml of solubilization/wash buffer supplemented with 300 ng/ml 3×Flag-Peptide. The purified sample was concentrated and buffer exchanged to a final volume of 0.5-1.0 ml in 20 mM HEPES, pH 7.3, 100 mM NaCl, 1% octylglucoside, 1% glycerol. Protein concentrations were determined using the DC Protein Assay. The concentration of the final Flag eluate was determined from the absorbance at 280 nm using an extinction coefficient of 193045 cm$^{-1}$M$^{-1}$. Samples of the final purified fraction were subjected to SDS-PAGE and silver staining.

In vitro palmitoylation was assayed according to Buglino, J. A. and Resh, M. D. "Hhat is a palmitoylacyl transferase with specificity for N-palmitoylation of sonic hedgehog". *J. Biol. Chem.* 283, 22076-22088 (2008) The in vitro assay was performed by incubating 10 µL of HhatHAFlagHis in 20 mM HEPES, pH 7.3, 100 mM NaCl, 1% octylglucoside, 1% glycerol with 10 µl of recombinant Shh (0.2-0.4 mg/mL in 20 mM MES, pH 6.5, 1 mM EDTA, 1 mM DTT), followed by the addition of 30 µL of reaction buffer (167 mM MES, pH 6.5, 1.7 mM DTT, 0.083% Triton X-100, 167 µM $^{125}$I-iodo-palmitate CoA). The reaction was stopped by the addition of 50 µL of 2× sample buffer with 40 mM DTT. Samples were electrophoresed on 12.5% SDS-PAGE gels, which were stained with Coomassie Blue, dried and exposed to phosphorimager for 12-18 hrs. After phosphorimaging, each Shh containing gel band was excised. $^{125}$I-iodo-palmitate incorporation was measured by counting in a Perkin-Elmer Gamma counter. Non-enzymatic incorporation of $^{125}$I-iodo-palmitate into Shh was corrected for by subtraction of counts from matched pcDNA 3.1 mock purification controls.

C-terminally biotinylated peptides corresponding to the first 10 amino acids of Shh (CGPGRGFGKR), N-terminal acetylated Shh (Acetyl-CGPGRGFGKR) and C24A Shh (AGPGRGFGKR) were synthesized by the Sloan-Kettering Microchemistry Core Facility. Purified peptides were palmitoylated in vitro as outlined above except that the final Shh peptide concentration was 100 µM. After incubation, 400 µL of RIPA buffer and 50 µl of Streptavidin-agarose beads were added, and the mixture was incubated for 1 hr at 4° C. with continuous mixing. Biotinylated peptides were pelleted by centrifugation at 1000×g for 5 minutes. Pellets were washed twice with 500 mL RIPA buffer. $^{125}$I-iodo-palmitate incorporation was determined by Gamma counting. Samples were incubated in either 1M Tris, pH8.0, or hydroxylamine, pH 8.0 for 1 hr at room temperature followed by 2 washes in RIPA buffer.

To show knockdown of Shh and Hhat in human pancreatic cancer cells, shRNAs directed against human Shh or Hhat were cloned into the pLKO1 vector. Human pancreatic cancer cell lines Panc1 and AsPC1 were transfected and selected for 10-14 days in puromycin. Analyses of Shh and Hhat mRNA levels were performed by RT-qPCR. The results established that knockdown of either Shh or Hhat inhibits both anchorage-dependent and anchorage-independent cell growth.

Figure 1:
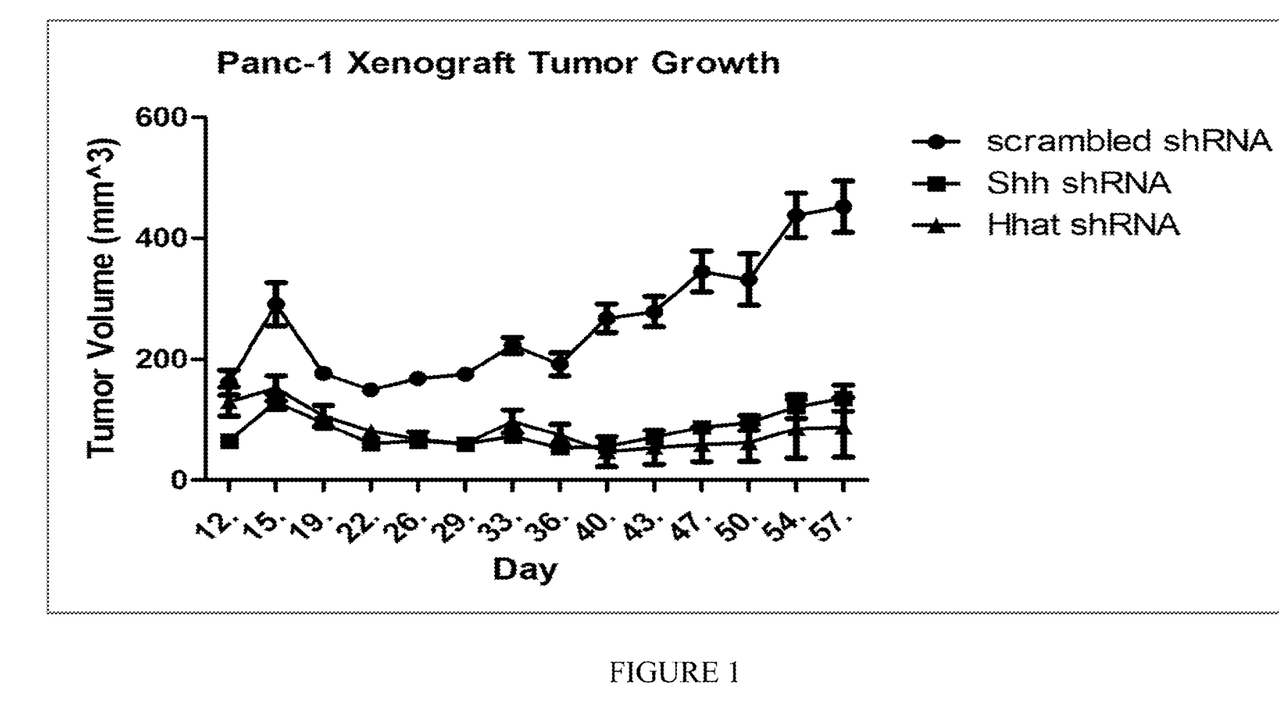
FIG. 1 depicts a graph of tumor volume versus time comparing cells in which Shh and Hhat have been suppressed with control cells.

Xenograft experiments were performed under Animal Protocol #11-02-003. Panc-1 cells were transfected with pLKO.1 encoding shRNAs directed against Shh, Hhat, or a scrambled (Scr) control. pLKO.1 is a lentivirus-based vector (Open Biosystems) that does not replicate, is self-inactivating, and is designed to deliver silencing shRNAs to tissue culture cells. Cells were grown in tissue culture for 10 days to allow for knockdown of the designated gene. Aliquots of cells were analyzed by RT-qPCR analysis to verify that >80% knockdown of Shh or Hhat had been achieved. A separate culture of Panc-1 cells that were not treated (Untr) with pLKO.1 were maintained as a control for any effect of pLKO.1 on tumor growth. Fifteen million Panc-1 cells were injected into the flanks of athymic (nude) female mice. Tumor measurements were taken with a caliper twice a week and plotted. The results are shown in FIG. 1. At the end of 71 days, tumor mass in the Shh or Hhat-depleted cells was less than 30% of control, showing that inhibition of Shh or Hhat correlates with tumor suppression.

Hhat activity assay: Five µl of 10 mM MES, pH 6.5 buffer was dispensed within each well of a 384-well white/clear-bottom plate (Greiner Bio-One, Kremsmuenster, Austria) using a Thermo Multi-Drop Combi dispenser. Compounds (12.5 µM final concentration) were dispensed using a Janus "Varispan" automated syringe pipette. Next, 3 µL of P100 membranes from HA-Hhat transfected 293FT cells were dispensed with the Thermo Multi-Drop Combi dispenser, and incubated for 20 min at room temperature. The reaction was started by the addition of 12 µL of reaction buffer (167 mM MES, pH 6.5, 2 mM DTT, 0.083% Triton X-100, 8.3 µM 125-I-iodo-palmitoylCoA, 5.21 µM Shh biotinylated peptide). Following a 1 hour incubation at room temperature, the reaction was stopped by the addition of 70 µL SPA beads solution (7.14 mg/mL in RIPA buffer), and the signal was detected on a Microbeta Trilux reader. Each plate included high control (DMSO only) and low control (0.125% TFA final concentration) rows. Percent inhibition for each experimental point was determined by the formula: [(high control−compound)/(high control−low control)]*100.

Human pancreatic adenocarcinoma cell assay: 5000 AsPC1 (human pancreatic adenocarcinoma) cells were plated in each well of a 384-well black/clear-bottom tissue culture plate (Greiner Bio-One, Kremsmuenster, Austria), using Thermo Multi-Drop Combi dispenser. The plates were incubated at 37° C. for 24 h before compounds were dispensed using a Janus "Varispan" automated syringe pipette at 50 µM final concentration. High control (DMSO only) and low control (cell media only) rows were included in each plate. After 48 h incubation, Alamar Blue (Invitrogen) was added to each well in 1:100 ratio. 4 h later, cell viability was assessed by measuring fluorescence on a Perkin-Elmer EnVision plate reader.

Compounds tested and found effective were:

| Example number | RU number | Structure | % Inhibition of Hhat at 12.5 µM |
|---|---|---|---|
| 1 | RU-0072298 | | 100.8 |

-continued

| Example number | RU number | Structure | % Inhibition of Hhat at 12.5 μM |
|---|---|---|---|
| 2 | RU-0072503 | | 98.9 |
| 3 | RU-0072407 | | 97.8 |
| 4 | RU-0072417 | | 96.2 |
| 5 | RU-0072436 | | 95.6 |
| 6 | RU-0072279 | | 94.7 |

-continued

| Example number | RU number | Structure | % Inhibition of Hhat at 12.5 μM |
|---|---|---|---|
| 7 | RU-0072513 | | 94.3 |
| 8 | RU-0072523 | | 94.3 |
| 9 | RU-0072130 | | 92.8 |
| 10 | RU-0072467 | | 91.6 |
| 11 | RU-0072268 | | 87.2 |

-continued

| Example number | RU number | Structure | % Inhibition of Hhat at 12.5 μM |
|---|---|---|---|
| 12 | RU-0072288 | | 17.1 |
| 13 | RU-SKI 101 | | |
| 14 | RU-SKI 201 | | |

Figure 2:
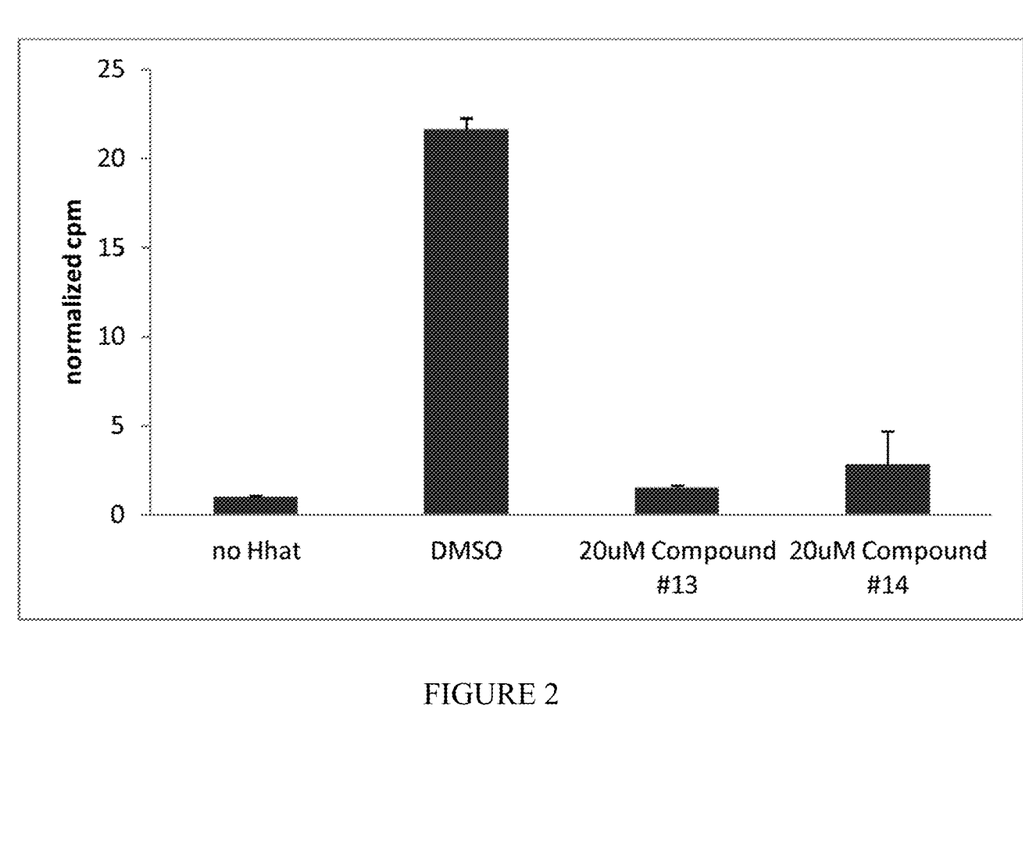
FIG. 2 depicts a bar graph showing counts per minute of radiolabeled palmitate residue incorporated into Shh peptide with controls and in the presence and absence of compounds 13 and 14.

Each of compounds 13 and 14 (20 μM) was incubated with purified Hhat in the presence of saturating concentrations of $^{125}$I-Iodopalmitoyl CoA+Shh peptide as described above. Radiolabeled peptides were pulled down with streptavidin agarose and the cpm incorporated into the peptide was quantified in a gamma counter. As shown in FIG. 2, compounds 13 and 14 are good inhibitors of Hhat activity, showing greater than 75% reduction in cpm.

Figure 3:
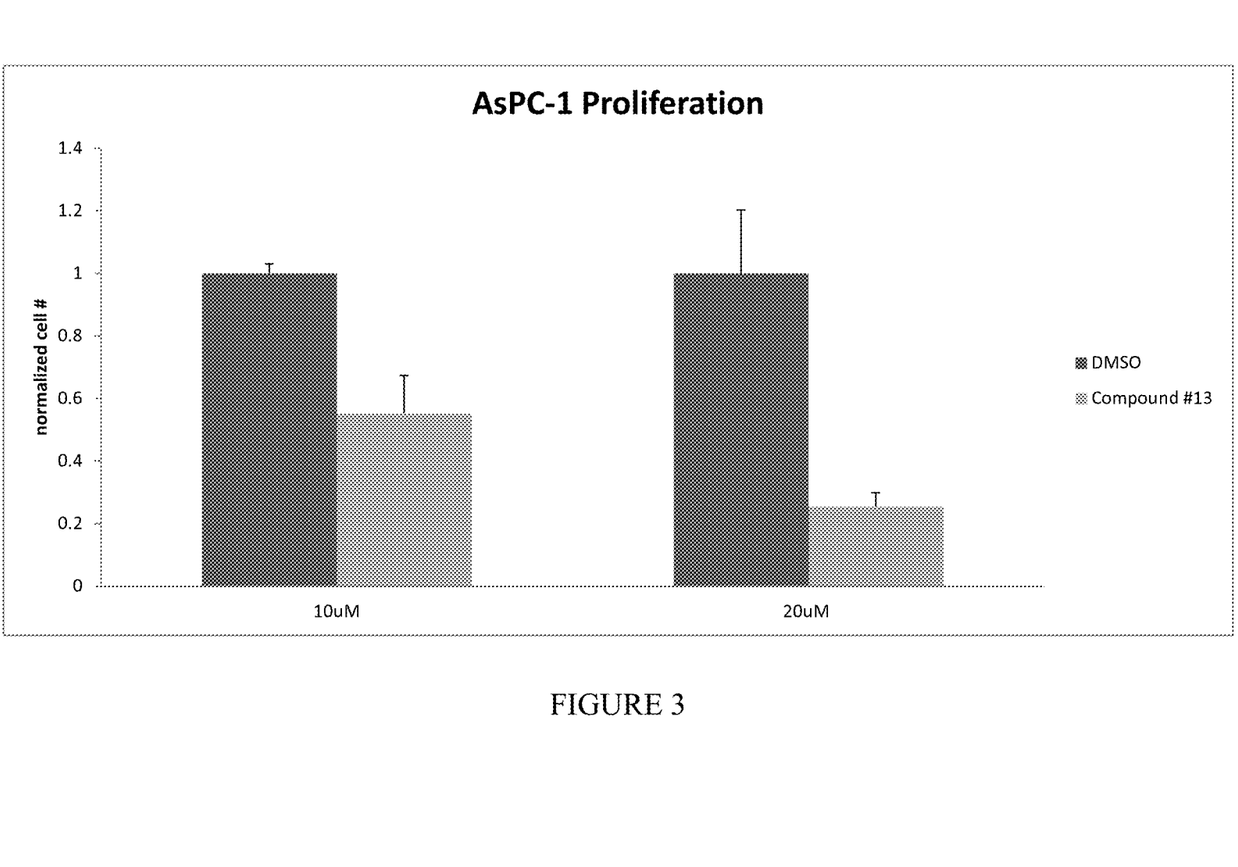
FIG. 3 depicts a bar graph showing cell counts of human pancreatic cancer cells in the presence and absence of compound 13.

Compound 13 was tested in the human pancreatic adenocarcinoma cell assay. The results are shown graphically in FIG. 3. At 10 μM it reduced the proliferation of human pancreatic cancer cells 50% at day six. At 20 μM it reduced the proliferation of human pancreatic cancer cells by 70% at day six.

IC50 values were generated for compound 13 (RU-SKI 101) and compound 14 (RU-SKI 201) in an in vitro Hhat activity assay at saturating substrate concentrations, using purified enzyme, 0.7 μM ShhN recombinant protein and 18 μM $^{125}$I-iodo-palmitoylCoA. The samples were incubated and incorporation into ShhN protein was quantified. Each experiment was repeated twice. The IC50 value for compound 13 was 2.05 μM and for compound 14 was 0.68 μM.

The invention claimed is:

1. A compound of the formula:

or a pharmaceutically acceptable salt thereof; wherein:
- $R^1$ and $R^2$ are independently hydrogen, halogen, $(C_1\text{-}C_4)$ hydrocarbyl, $(C_1\text{-}C_4)$alkoxy, trifluoromethyl, trifluoromethoxy, cyano, or nitro;
- $R^3$ is $(C_1\text{-}C_{10})$hydrocarbyl, $(C_1\text{-}C_6)$oxaalkyl, or heterocyclylalkyl;
- $R^4$ is hydrogen, methyl, halomethyl, dihalomethyl, or trihalomethyl; and
- A is a 5- or 6-membered aromatic heterocycle.

2. The compound according to claim 1, wherein A is pyrrolidine, furan, thiophene, or pyridine.

3. The compound according to claim 2, wherein A is pyridine.

4. The compound according to claim 1, wherein $R^1$ is hydrogen or methyl; and $R^2$ is hydrogen, methyl, methoxy, chloro, or fluoro.

5. The compound according to claim 4, wherein $R^1$ is hydrogen; and $R^2$ is methyl.

6. The compound according to claim 4, wherein $R^1$ is hydrogen; and $R^2$ is hydrogen.

7. The compound according to claim 1, wherein Ring A is a 6-membered aromatic heterocycle; and $R^1$ is meta relative to the point of attachment of Ring A to the thieno[3,2-c]pyridine, wherein $R^1$ is halogen, $(C_1\text{-}C_4)$hydrocarbyl, $(C_1\text{-}C_4)$alkoxy, trifluoromethyl, trifluoromethoxy, cyano, or nitro.

8. The compound according to claim 7, wherein $R^1$ is halogen.

9. The compound according to claim 8, wherein $R^2$ is hydrogen, methyl, methoxy, chloro, or fluoro.

10. The compound according to claim 7, wherein $R^1$ is methyl.

11. The compound according to claim 8, wherein $R^2$ is hydrogen, methyl, methoxy, chloro, or fluoro.

12. The compound according to claim 1, wherein $R^3$ is $(C_1\text{-}C_{10})$alkyl.

13. The compound according to claim 12, wherein $R^3$ is $(C_3\text{-}C_6)$alkyl.

14. The compound according to claim 1, wherein $R^3$ is $(C_3\text{-}C_6)$alkyl, $(C_3\text{-}C_6)$alkenyl, $(C_3\text{-}C_6)$cycloalkyl, $(C_1\text{-}C_6)$oxaalkyl, furanyl$(C_1\text{-}C_4)$alkyl, thienyl$(C_1\text{-}C_4)$alkyl, pyrrolyl$(C_1\text{-}C_4)$alkyl, pyrrolidinyl$(C_1\text{-}C_4)$alkyl, or tetrahydrofuranyl$(C_1\text{-}C_4)$alkyl.

15. The compound according to claim 1, wherein $R^3$ is methoxyethyl, methoxypropyl, ethoxypropyl, isopropyl, cyclopropyl, allyl or furanylmethyl.

16. The compound according to claim 1, wherein $R^3$ is of the formula:

17. The compound according to claim 1, wherein $R^4$ is hydrogen.

18. The compound according claim 1, of the formula:

or a pharmaceutically acceptable salt thereof.

19. A pharmaceutical composition comprising a compound of claim 1, or a pharmaceutically acceptable salt thereof, and a pharmaceutically acceptable carrier.

20. A pharmaceutical composition comprising a compound of claim 18, or a pharmaceutically acceptable salt thereof, and a pharmaceutically acceptable carrier.

* * * * *

SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1

Cys Gly Pro Gly Arg Gly Phe Gly Lys Arg

```
<210> SEQ ID NO 2
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: ACETYLATION

<400> SEQUENCE: 2

Cys Gly Pro Gly Arg Gly Phe Gly Lys Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3

Ala Gly Pro Gly Arg Gly Phe Gly Lys Arg
1               5                   10
```

UNITED STATES PATENT AND TRADEMARK OFFICE
CERTIFICATE OF CORRECTION

PATENT NO. : 9,943,507 B2
APPLICATION NO. : 15/459911
DATED : April 17, 2018
INVENTOR(S) : Marilyn D. Resh et al.

Page 1 of 1

It is certified that error appears in the above-identified patent and that said Letters Patent is hereby corrected as shown below:

In the Specification

At Column 1, Lines 23-26, the text:
"This invention was made with Government support under Contracts Nos. GM57966 and CA158474, awarded by the National Institutes of Health. Accordingly, the U.S. Government has certain rights in this invention."

Should be replaced with the text:
-- This invention was made with government support under CA158474 and GM057966 awarded by the National Institutes of Health. The government has certain rights in the invention. --

Signed and Sealed this
Nineteenth Day of May, 2020

Andrei Iancu
*Director of the United States Patent and Trademark Office*